(12) United States Patent
Stec et al.

(10) Patent No.: US 10,285,648 B2
(45) Date of Patent: May 14, 2019

(54) MULTIFUNCTIONAL, ELECTROPHYSIOLOGICAL DIAGNOSTIC CATHETER FOR TREATMENTS IN ELECTROCARDIOLOGY

(71) Applicant: Medinice S.A., Kielce (PL)

(72) Inventors: Sebastian Stec, Warsaw (PL); Sanjeev Choudhary, Warsaw (PL)

(73) Assignee: MEDINICE S.A., Kielce (PL)

( * ) Notice: Subject to any disclaimer, the term of this patent is extended or adjusted under 35 U.S.C. 154(b) by 698 days.

(21) Appl. No.: 14/763,227

(22) PCT Filed: Mar. 12, 2015

(86) PCT No.: PCT/IB2015/051815
§ 371 (c)(1),
(2) Date: Jul. 24, 2015

(87) PCT Pub. No.: WO2016/071779
PCT Pub. Date: May 12, 2016

(65) Prior Publication Data
US 2016/0302728 A1    Oct. 20, 2016

(30) Foreign Application Priority Data
Nov. 7, 2014 (PL) .......................... 410085

(51) Int. Cl.
*A61B 5/042* (2006.01)
*A61B 5/00* (2006.01)
(Continued)

(52) U.S. Cl.
CPC .......... *A61B 5/6853* (2013.01); *A61B 5/0215* (2013.01); *A61B 5/0422* (2013.01);
(Continued)

(58) Field of Classification Search
CPC . A61B 5/6853; A61B 5/0422; A61B 18/1492; A61B 2017/22051; A61B 2018/00285
See application file for complete search history.

(56) References Cited

U.S. PATENT DOCUMENTS 3,995,623 A * 12/1976 Blake ................ A61B 5/02158
600/381
4,961,738 A    10/1990 Mackin
(Continued)

FOREIGN PATENT DOCUMENTS

EP    363 156 A2    4/1990
EP    1011437 B1    5/2006

*Primary Examiner* — Lee S Cohen
*Assistant Examiner* — Erin M Cardinal
(74) *Attorney, Agent, or Firm* — Craft Chu PLLC; Andrew W. Chu

(57) ABSTRACT

The multifunctional, electrophysiological diagnostic catheter for electrocardiologic treatments includes a distal end, diagnostic rings, a balloon, a main channel, a manipulation handgrip, functional connection and internal channels. There is an internally-located open central channel, wherein inlet/outlet of an internal channel is located in the distal ring. There is a pumping channel for pumping up and pumping out of the occlusion-stabilizing balloon located after the diagnostic rings. There is a division of a central channel into two branches in the region of the catheter proximal end.

10 Claims, 3 Drawing Sheets

(51) Int. Cl.
*A61B 5/0215* (2006.01)
*A61B 5/15* (2006.01)
*A61B 5/153* (2006.01)
*A61B 34/20* (2016.01)
*A61M 25/00* (2006.01)
*A61M 25/10* (2013.01)

(52) U.S. Cl.
CPC .......... *A61B 5/15003* (2013.01); *A61B 5/153* (2013.01); *A61B 5/150221* (2013.01); *A61B 5/150992* (2013.01); *A61B 34/20* (2016.02); *A61M 25/0026* (2013.01); *A61M 25/1002* (2013.01); *A61B 5/15* (2013.01); *A61B 5/150229* (2013.01); *A61B 2562/17* (2017.08)

(56) References Cited

U.S. PATENT DOCUMENTS

| | | | | |
|---|---|---|---|---|
| 5,496,271 | A * | 3/1996 | Burton | A61B 18/18 604/101.05 |
| 5,500,012 | A * | 3/1996 | Brucker | A61B 5/0422 604/22 |
| 5,505,701 | A * | 4/1996 | Anaya Fernandez de Lomana | A61B 5/0422 604/101.03 |
| 7,306,589 | B2 * | 12/2007 | Swanson | A61B 18/02 606/20 |
| 2003/0149468 | A1 * | 8/2003 | Wallsten | A61M 25/104 623/1.11 |
| 2004/0111016 | A1 * | 6/2004 | Casscells, III | A61B 5/01 600/310 |
| 2004/0162485 | A1 * | 8/2004 | Wendlandt | A61B 1/00094 600/424 |
| 2006/0009758 | A1 * | 1/2006 | Edwards | A61B 18/00 606/41 |
| 2006/0287604 | A1 * | 12/2006 | Hickey | A61B 5/02158 600/508 |
| 2008/0161795 | A1 * | 7/2008 | Wang | A61B 18/18 606/41 |
| 2010/0010488 | A1 * | 1/2010 | Kassab | A61B 18/1492 606/41 |
| 2010/0198040 | A1 | 8/2010 | Friedman | |
| 2010/0331658 | A1 * | 12/2010 | Kim | A61B 18/1492 600/373 |
| 2011/0098561 | A1 * | 4/2011 | Thornton | A61M 25/0054 600/431 |
| 2013/0237817 | A1 * | 9/2013 | Mihaljevic | A61B 1/00085 600/435 |
| 2013/0304047 | A1 * | 11/2013 | Grunewald | A61B 18/1815 606/14 |
| 2014/0257271 | A1 * | 9/2014 | Mayse | A61B 18/1492 606/34 |
| 2015/0112172 | A1 * | 4/2015 | Atlee | A61B 5/1459 600/325 |
| 2015/0141982 | A1 * | 5/2015 | Lee | A61B 5/6858 606/41 |
| 2015/0272669 | A1 * | 10/2015 | Brucker | A61B 18/1492 606/41 |

* cited by examiner

MULTIFUNCTIONAL, ELECTROPHYSIOLOGICAL DIAGNOSTIC CATHETER FOR TREATMENTS IN ELECTROCARDIOLOGY

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The object of the invention is a multifunctional, electrophysiological diagnostic catheter used for treatments in electrocardiology consisting of stabilization balloon, especially for stabilization of a catheter in a coronary sinus.

2. Description of Related Art Including Information Disclosed Under 37 CFR 1.97 and 37 CFR 1.98.

Rapid diagnosis and fast treatment of potentially dangerous arrhythmia allows for significant reduction of patients' morbidity for patients suffering from cardiac arrhythmia, which leads in its most serious form to sudden cardiac death. One of diagnostic method used for cardiac arrhythmia diagnosis is invasive electrophysiological study (EPS), using diagnostic catheters. Reliable identification of cardiac arrhythmia substrate and continuous, precise monitoring of rhythm and catheter electrodes localized intracardiacly are essential.

Catheters equipped with balloons are known from the state of the art. In application, U.S. Pat. No. 3,995,623 shows that there is the catheter described with a flow balloon on its distal end passing through right vestibule, right ventricle, and to the pulmonary artery. Clearance in tubule of catheter is open on the distal end in order to monitor blood pressure in the pulmonary artery or branch, or to obtain blood sample. A thermistor closer to the balloon enables measurement of blood temperature in this region, thus enabling identification of cardiac output using termodilution technique. A second tubule comprises a gap, which is characteristically located in junction region of vena cava and right vestibule, in order to monitor pressure, infusion of liquid media and blood sampling. Besides these two mentioned channels, a third stream is used as a channel for pumping the balloon, and a fourth stream, which comprises thermistor wires, is for distal and proximal electrodes.

Patent No. JP2893833 discloses an endoscopic electrode comprising balloon, which is installed on the front end of tube made of synthetic resin, surrounding a rim of a front pipe and ending in a way to avoid gap closure. Part of the front end connecting with one tube clearance and recess are made by external surface of tube, and the balloon can be communicated with one tube clearance delivering lateral gap to the tube interior or through excision of front tube part. An optical fiber is located in the clearance, and distance between fiber and inner surface of lumen is used as a passage for balloon expansion liquid. The balloon acts as a stabilizer, because even if saline is not used to fill balloon, the catheter position is not changed, and observation or diagnostics can be performed.

US2008097297 is an application describing a medical product, which is able to penetrate blood vessels comprising at least one non-expandable piercing element fitted and configured for specific local activity in vivo e.g. diagnosis, sampling, energy therapy and drug administration. This device additionally comprises at least one inflatable balloon used for local positioning, which is configured for safe placement of device around target tissue of human vessels or internal organs.

EA009756 B1 is an application disclosing a catheter comprising three elastic channels, wherein, first, an internal one delivers fluid for balloon filling, an external is used as a support of balloon localization, and a lateral channel is for lymph sampling. Annular-shaped elastic balloons are equipped with threads for catheter installation in clearance of a venous angle, where an elliptically-shaped elastic balloon is equipped with a trigger plate for a contact with lymph outlet. In case of lymph sampling, placement of the catheter in an operating position in the venous angle depression is required, obtaining growth in volume through increasing elastic balloon volume by injection of saline inside.

Also other solutions are known, which mention a possibility of blood flow blockade e.g. EP0363156, which is an application referring to an apparatus for volumetric blood measurement in vessel with walls characterized in that an elastic catheter is adapted for placement in a vessel and comprises ultrasound sensors. This apparatus is equipped with a device for pressure measurement in right atrium, pressure in pulmonary artery and wedge pressure. Volumetric flow is determined using termodilution.

WO9806450 is an application disclosing a catheter-type device for hemorrhage control during closed surgery. In the end of catheter, there is an inter alia balloon adapted for movement with an elastic catheter along a blood vessel, wherein a pump-enabling channel is located, which makes it possible for fast balloon inflating (filling) and emptying. When a precise balloon location in a surrounding of a blood vessel is confirmed, the balloon is located in the flow in order to close blood flow and prevent hemorrhage in a designated region of surgical intervention. Magnetic material is attached to the aforementioned balloon for magnetic coupling and balloon positioning by manipulation using a magnet located outside of the blood vessel. The catheter can be equipped with a channel adapted for blood sampling and drug delivery.

In the state of art, there are catheters known by which it is possible to take a blood sample.

U.S. Pat. No. 5,607,389A relates to a medical device comprising the probe, cover for the probe, and microdevice for placement, e.g. biopsy sampler for tissue sampling as a needle or sharp end in order to facilitate the sampler reaching out to proper tissue or the sampler having a shape similar to a harpoon or jaws. Further embodiments include a knife sampler and electromagnetic transmitter for selective sample collection and electromagnetic ablative heating.

EP1145731 discloses a multilumenal, multipurpose catheter set comprising multiple axis channels, wherein at least one channel supports other functionality than material delivery and material removal, which left after its delivery. The catheter can comprise at least two individual channels parallel to a middle catheter cylinder. Two channels are used for sampling of fluids from that body part, where the catheter is placed.

Solutions known from the state of the art do not allow for universal connection of all diagnostic functions (measurement of heart potentials, localization and navigation without fluoroscopy, selective blood sampling from suitable vessel or heart cavity localized using catheter ending, possibility of selective delivery of substance or contrast localized using catheter ending and catheter stabilization and blood flow blocking in blood vessel using balloon).

In any of the described solutions, catheter stabilization in a coronary cavity and blockade of fluid flow through coronary sinus was not mentioned. Objective solutions based on connection of multiple functionalities utilized by one catheter-electrode, give the operator new and useful possibilities.

SUMMARY OF THE INVENTION

The subject matter of the invention is a multifunctional, electrophysiological diagnostic catheter for treatment in electrocardiology, comprising a distal ending, diagnostic rings, balloon, main tube, manipulation handgrip, functional switches, and internal channels. The catheter is characterized in that it comprises:
- an internally located open central channel, wherein the inlet/outlet of central channel is located in a distal ring;
- a channel for pumping up and pumping out of occlusion-stabilizing balloon;
- an occlusion-stabilizing balloon located after diagnostic rings; and
- a division of central channel in area of proximal catheter ending on two branches.

Preferably, the central channel is unobstructed in both ways.

Preferably, the inlet/outlet of central channel is round, wherein it is located in a recess, which is located centrally in the distal ring.

Preferably, a recess 1.1 has smooth, round, atraumatic edges 1.2.

Preferably, the central channel is a flow channel for fluids.

Preferably, the central channel is a transmission channel for introduction of microdevices and/or microelectrodes.

Preferably, the central channel is a compartment for selective drug administration or contrast agent or saline or blood sampling.

Preferably, the multi-purpose catheter performs measurement of blood pressure.

Preferably, the occlusion-stabilizing balloon with modifiable diameter assumes a shape ranging from spherical to ellipsoidal.

Preferably, the occlusion-stabilizing balloon is filled with air or saline.

Preferably, the multi-purpose catheter is guided and monitored using a system for electroanatomical mapping.

Preferably, in manipulation handgrip of multifunctional catheter, there is placed:
- an inlet/outlet for electric connections,
- an inlet/outlet for central channel, and
- an inlet/outlet for pumping/draining a channel of the occlusion-stabilizing channel.

Preferably, a proximal end of the central channel comprises a tee dividing proximal end of central channel on two branches, wherein one is ends with a diaphragm, while a second one comprises an opening/closing valve and end for connection of a pumping device, preferably syringe.

Preferably, the proximal end of the pumping channel comprises an end for connection of a pumping device, preferably syringe.

A multifunctional catheter is a universal reference, being stimulating, diagnostic and enabling to sample blood e.g. from a coronary sinus, peripheral and venous vessels type of catheter. In one catheter, there are few diagnostic features combined usually available in combination of two or three catheters (hemodynamic catheter, diagnostic, electrophysiological catheter, and a catheter with balloon).

The advantage of a multifunctional catheter is a very precise blood sampling depending on location of the catheter end, and also the fact, that it can be used for blood sampling from a vein or peripheral vessels from other organs e.g. cerebral circulation.

The advantage is also the use of a balloon for occlusion-stabilizing of the catheter in a coronary sinus or closing an examined venous vessel. Thanks to the catheter according to the invention, there is a possibility for precise, selective blood sampling from venous or peripheral vessels depending on catheter placement. The occlusion-stabilizing balloon prevents mixing of blood from coronary sinus outflow (blood from heart muscle) with blood localized in the right atrium (blood from body peripheries). Through inlet/outlet of central channel, it is possible to administrate contrast or blood sampling. It is also possible to administer an additional drug, perform pressure measurement or introduce other microdevices with diagnostic-therapeutic capabilities. Therefore, the catheter (its central channel) can be the transmission channel for atraumatic and selective introduction of microdevices and/or microelectrodes, which dimension and structure unable navigation and precise atraumatic introduction through venous system e.g. to cardiac cavities or coronary sinus.

The advantage is also introduction of a channel division outgoing from the manipulation handgrip. Channel division enables practical separation of catheter function on the electrophysiological end of the central channel and end for filling the system and draining of the stabilization balloon.

It selectively divides functions for operator service. From division, electrical connections come out, joining with an electric socket plugged to the connector, which is transmitting electroanatomical and electrophysiological system parameters. Additionally, the handgrip comprises a system controlling the catheter distal end, which is not a subject of the invention.

BRIEF DESCRIPTION OF THE DRAWINGS

The multifunctional catheter according to the invention was described in more details in exemplary embodiments and on the drawing.

DETAILED DESCRIPTION OF THE DRAWINGS

Figure 1:
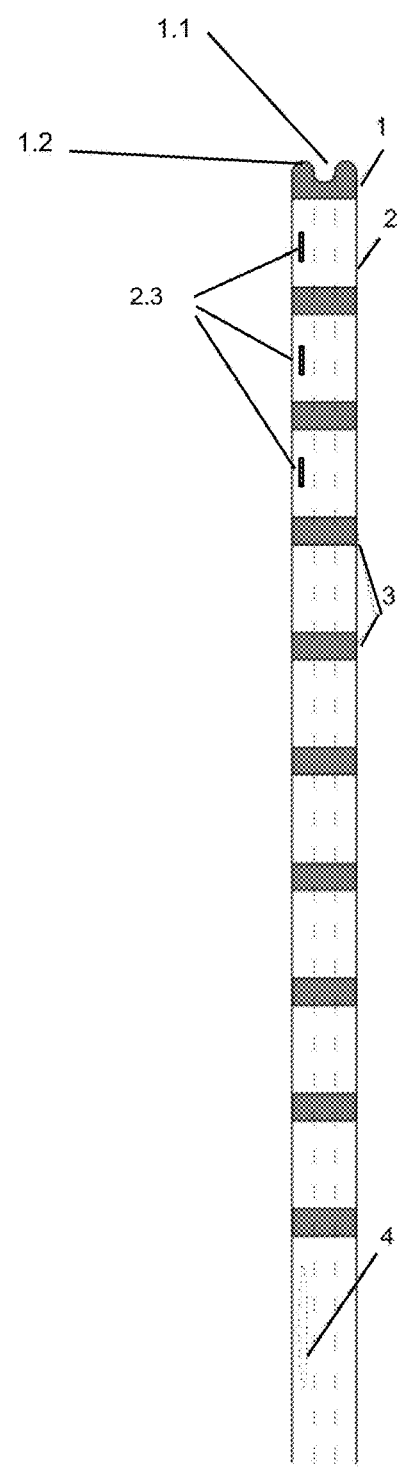
FIG. 1 shows a side elevation view of a main channel, a covering distal ring, diagnostic rings and a balloon.

The multifunctional catheter comprises manipulation handgrip 5, main channel or main tube 2, distal ring 1, occluding-stimulation balloon 4, diagnostic rings 3, and three connections: liquid connection 6 for contrast administration or blood sampling from coronary sinus or introduction of microdevices 6.2; pumping connection 7 for pumping up and pumping out of balloon with a pump 7.1 and compartment 7.2 of saline or air; and electric connection

8 for electrical wires 8.1 connecting diagnostic rings 3 and distal ring 1 with electrophysiological system.

The multifunctional catheter comprises two channels. Channel B is centrally located flow channel for liquids, which opens through the distal diagnostic ring 1 at an atraumatic ending of the catheter, as shown in FIG. 1. Pumping channel A is a channel used for filling and draining of occlusion-stabilizing balloon 4 through pumping connection 7 for liquid or gas pumping/draining from balloon. Balloon 4 is an expandable balloon made of elastic material.

Channel A and channel B are surrounded by electric wires connecting diagnostic rings 3 and distal ring 1 with manipulation handgrip 5 and transmitting electrophysiological parameters of electrophysiological system.

Additionally, in main channel 2, there are wires placed controlling distal end of catheter.

Proximal end of main channel 2, while connecting with manipulation handgrip 5 at the distal handgrip opening 5.1, divides into two channels (a first channel 2.1 and a second channel 2.2) and a cluster of electric wires. There are emerging branches or channels coming out from a proximal hand grip opening 5.2 of the manipulation handgrip 5 to liquid connection 6 of central channel B, pumping connection 7 for filling and draining of the occlusion-stabilizing balloon, and the electric connection 8.

Liquid connection 6 ends with tee 6.1 from which a first tee branch 6.3 is an extension of the central channel and creates a proximal end of the central channel and is equipped with a diaphragm 6.7 enabling introduction of microdevices 6.2, such as a blood pressure measurement device, without liquid leakage. A second tee branch 6.4 is equipped with a valve 6.8 and an ending for a pump 6.5 and compartment 6.6, such as a syringe.

Pumping connection 7 is equipped with a valve and an ending for a syringe, which is used for balloon pumping up and pumping out 4.

Electric connection 8 creates electric socket, which is connected with an electrophysiological system through a connector.

Figure 2:
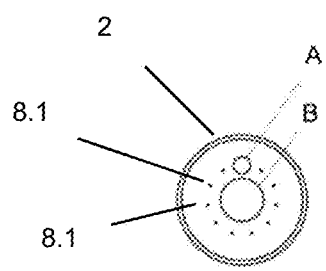
FIG. 2 shows a cross-sectional view of the main channel of the multifunctional catheter.
Figure 3:
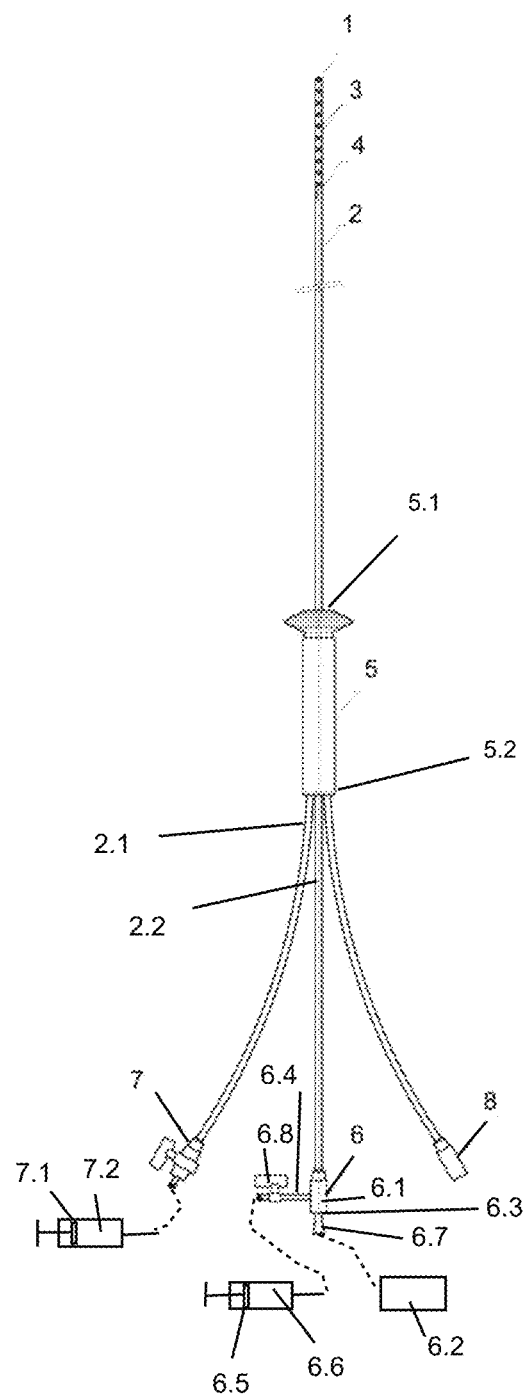
FIG. 3 shows a side elevation view of the multifunctional diagnostic catheter with the manipulation handgrip and functional connections.

The inlet/outlet of central channel B is located in a distal ring of the catheter and is shaped atraumatically, what means that the edges are smooth and curved as shown in FIG. 2. Besides, there is a gap placed below external walls. Sharp edges could break the blood vessels continually and increase perforation risks.

The multifunctional diagnostic catheter comprises diagnostic rings 3 present in an amount of 4 to 20 (default 10) for analysis of electric parameters of heart and vessels evenly distributed on length of 6 to 14 cm. These rings are located in the vicinity of distal and of catheter. In a preferred embodiment, diagnostic rings are used as rings visible under X-ray or in system of non-fluoroscopic navigation and mapping.

On the distal end of the catheter, there is also occlusion-stabilizing balloon 4 present, which is placed after diagnostic rings 3 and which enables selective blockage of blood flow in an intubated vessel.

In a vicinity of the main channel of the proximal end, there is a manipulation handgrip present, where channel division occurs. Division of catheter channels and electric wires enables interchangeable usage of a liquid dosing device in case of drug administration, contrast agent, or suction device in case of blood sampling. Channel division enables easy separation of main channel component functions and its redirection to connections going out of the proximal part of handgrip. The multifunctional catheter is made of elastic material enabling its easy bending, and the distal end is equipped with a control system localized in the catheter handgrip and connected with a proper ties.

The catheter is finally positioned using X-rays, analysis of electric potentials or using a non-fluoroscopic three dimensional electroanatomical system. Subsequently, occlusion-stabilizing balloon 4 is pumped up in order to stabilize catheter position in vessel in a proximal end of a coronary sinus. To the central channel B, a blood sample is taken, sucked using a low-pressure suction device (syringe), and, after passage through a distributor and disconnection of the suction device, and is poured into the test-tube. In a case when there is a need to administer a drug, contrast or other medical agent to a specific heart region or vessels, liquid connection 6 is connected to the pumping device (syringe) and through a distributor and next through the central channel B, a medical agent is administered. Between activities described above, there is a need for central channel B to be flushed using saline solution.

Through central channel B, there is a possibility of microdevice introduction e.g. MicroCosinus electrode for ultrasonography, to the heart regions, which can be used for blood vessels diagnostics with a small diameter.

In a preferred embodiment it is possible to measure blood pressure in a chosen region of heart or vessels based on connection to the liquid connection 6.

A catheter with occlusion-stabilizing balloon 4 in a drained state is introduced to the patient's peripheral vein vessels (femoral vein, subclavian vein) and is further passed through main vessels to right cardiac cavities. A control system 2.3 enables bending of the catheter distal end, which permits localization of coronary sinus outflow. Navigation and localization of the catheter position can be performed based on catheter translucency in X-rays or based on analysis of potentials and electrophysiological parameters by a three-dimensional system and non-fluoroscopic navigation (without X-rays). A catheter, thanks to diagnostic rings 3, enables continuous registration of potentials and construction of virtual electroanatomical map giving an image of examined vessels and cardiac cavities. When an operator reaches his goal, so when he gets to his desirable location, occlusion-stabilizing balloon 4 is pumped up and can become an electrode-stabilizing system in a coronary sinus (reducing risk of the electrode falling out during patient's heart stoppage or breathing movement). Additionally stable electrode localization enables stable and precise building of cardiac cavities contours and use of intracardial electrode as a marker/reference point for other points in created virtual map of heart. Additionally, a balloon can, in a precise manner, prevent blood from mixing from a coronary sinus with blood coming from the right vestibule, which enables reliable and selective blood sampling from the catheter end.

Blood is sampled using a syringe connected to the liquid connection 6 protected by a valve. Gap in liquid connection 6 for substance administration or blood sampling can be also used for drug administration, pressure measurement. Gap on the proximal end of central channel B is ended with a gate (diaphragm), through first tee branch 6.3 which enables introduction of microdevices with an additional diagnostic-therapeutic functions e.g. MicroCosinus electrode with a diameter below 2 mm for electrophysiological diagnostics of vessel with a very small diameter. Pressure measurement can be registered using liquid connection 6 or using microdevice for pressure measurement introduced through gap on proximal end of central channel.

Diagnostic rings 3 distributed in distance 6 to 14 cm from distal ring 1 of catheter enable registration of electrophysiological parameters (shape and amplitude of mono- and bipolar electric potential, impedance), selective stimulation using external stimulator or non-fluoroscopic navigation using three-dimensional system.

Occlusion-stabilizing balloon 4 is filled using saline solution and performs stabilizing and blocking functions for flow in coronary sinus.

We claim:

1. A multifunctional electrophysiological diagnostic catheter for electrocardiology, the catheter comprising:
    a main tube 2 being flexible in a deployed configuration and having a distal end and a proximal end;
    a control system 2.3 connected to said distal end so as to bend said distal end;
    a plurality of diagnostic rings 3 on said main tube, wherein at least one diagnostic ring is a distal diagnostic ring 1 at said distal end of said main tube;
    a manipulation handgrip 5 on said main tube adjacent said proximal end;
    a balloon 4 within said main tube between said diagnostic rings and said manipulation handgrip,
    wherein said balloon is placed after said plurality of said diagnostic rings from said distal end of said main tube, said distal end of said main tube and said plurality of diagnostic rings being in a bent position independent from said balloon, when said balloon is in an inflated configuration,
    wherein said main tube is comprised of:
        a central channel B being centered within said main tube and having a central proximal opening at said proximal end and a central distal opening at said distal end, said distal diagnostic ring being positioned at said distal opening;
        a plurality of electrical wires 8.1 around said central channel; and
        a pumping channel A being in fluid connection with said balloon, being aligned with said electrical wires, said electrical wires and said pumping channel forming a circle around said central channel, and having a pumping proximal opening at said proximal end and a pumping distal opening connected to said balloon;
    a first channel 2.1 being connected to said pumping proximal opening and being in fluid connection with said pumping channel; and
    a second channel 2.2 being in fluid connection with said central channel and connected to said central proximal opening of said central channel,
    wherein said second channel is in fluid connection with said distal opening at said distal end of said main tube through said central proximal opening, and
    wherein said distal diagnostic ring is comprised of a central recess 1.1, said distal opening being connected to said central recess, said central recess having smooth round edges 1.2.

2. The multifunctional catheter, according to claim 1, further comprising: a microdevice 6.2 in fluid connection with said central channel through said second channel connected to said central proximal opening at said proximal end.

3. The multifunctional catheter, according to claim 1, further comprising: a pump 6.5 and a compartment 6.6 containing a liquid, said compartment being in fluid connection with said central channel through said second channel connected to said central proximal opening at said proximal end.

4. The multifunctional catheter, according to claim 1, further comprising: a blood pressure measurement device 6.2' in fluid connection with said central channel through said second channel connected to said central proximal opening at said proximal end.

5. The multifunctional catheter, according to claim 1, wherein said balloon has a modifiable diameter and a shape ranging from spherical to ellipsoidal.

6. The multifunctional catheter, according to claim 5, wherein said modified diameter is set by at least one of a group consisting of air and saline filling said balloon.

7. The multifunctional catheter, according to claim 1, further comprising: a system for electroanatomic mapping in communication with said diagnostic rings.

8. The multifunctional catheter, according to claim 1, wherein said manipulation handgrip comprises:
    a distal handgrip opening 5.1 receiving said main tube; and
    a proximal handgrip opening 5.2, said first channel extending through said proximal handgrip opening, said second channel extending through said proximal handgrip opening, and said electrical wires 8.1 extending through said proximal handgrip opening.

9. The multifunctional catheter, according to claim 1, further comprising:
    a tee 6.1 dividing said second channel into a first tee branch 6.3 and a second tee branch 6.4;
    a diaphragm 6.7 in fluid connection with said first tee branch;
    a valve 6.8 connected to said second tee branch; and
    a connection for a pump 6.5 in fluid connection with said second tee branch.

10. The multifunctional catheter, according to claim 1, further comprising: a balloon pump 7.1 and a balloon compartment 7.2 containing a liquid, said balloon compartment being in fluid connection with said pumping channel through said first channel.

* * * * *